US011241012B2

(12) United States Patent
Montag et al.

(10) Patent No.: US 11,241,012 B2
(45) **Date of Patent: *Feb. 8, 2022**

(54) USE OF TETRAZOLINONES FOR COMBATING RESISTANT PHYTOPATHOGENIC FUNGI ON SOYBEAN

(71) Applicant: BASF SE, Ludwigshafen am Rhein (DE)

(72) Inventors: Jurith Montag, Limburgerhof (DE); Markus Gewehr, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/084,446

(22) PCT Filed: Mar. 14, 2017

(86) PCT No.: PCT/EP2017/055956

§ 371 (c)(1),
(2) Date: Sep. 12, 2018

(87) PCT Pub. No.: WO2017/157916

PCT Pub. Date: Sep. 21, 2017

(65) Prior Publication Data

US 2019/0069554 A1 Mar. 7, 2019

(30) Foreign Application Priority Data

Mar. 16, 2016 (EP) .................................... 16160603

(51) Int. Cl.
*A01N 43/713* (2006.01)
*C07D 403/12* (2006.01)

(52) U.S. Cl.
CPC ......... *A01N 43/713* (2013.01); *C07D 403/12* (2013.01)

(58) Field of Classification Search
CPC ............................ A01N 43/713; C07D 403/12
See application file for complete search history.

(56) References Cited

U.S. PATENT DOCUMENTS 2,526,660 A 10/1950 Craig et al.
4,242,121 A 12/1980 Hawkins et al.
4,599,362 A 7/1986 Nakatani et al.
4,940,720 A 7/1990 Nevill et al.
4,940,721 A 7/1990 Nevill et al.
4,945,100 A 7/1990 Nyfeler et al.
4,992,458 A 2/1991 Riebli et al.
5,143,932 A 9/1992 Jautelat et al.
5,162,358 A 11/1992 Jautelat et al.
5,215,747 A 6/1993 Hairston et al.
5,378,460 A 1/1995 Zuckerman et al.
5,501,852 A 3/1996 Meadows et al.
5,631,276 A 5/1997 Kern
5,747,025 A 5/1998 Meadows et al.
5,885,598 A 3/1999 Knauf et al.
6,060,051 A 5/2000 Heins et al.
6,871,446 B1 3/2005 Yamashita
7,183,299 B2 2/2007 Kobori et al.
7,714,140 B2 5/2010 Nagata et al.
8,318,636 B2 11/2012 Bais et al.
8,445,255 B2 5/2013 Kloepper et al.
8,609,667 B2 12/2013 Liu et al.
8,772,200 B2 7/2014 Shibayama et al.
8,865,759 B2 10/2014 Seitz et al.
9,078,447 B2 7/2015 Schoefl et al.
9,655,364 B2 5/2017 Matsuzaki
9,708,341 B2 7/2017 Wakamatsu et al.
9,781,931 B2 10/2017 Matsuzaki
9,781,932 B2 10/2017 Matsuzaki
9,789,131 B1 10/2017 Korinek et al.
2002/0152503 A1 10/2002 King et al.
2003/0068303 A1 4/2003 Selvig et al.
2003/0203131 A1 10/2003 Lemay
2003/0224936 A1 12/2003 Kretzschmar
2007/0244073 A1 10/2007 Angst et al.
2008/0108686 A1 5/2008 Gewehr et al.
2009/0036509 A1 2/2009 Gewehr et al.
2009/0286768 A1 11/2009 Crew et al.
2010/0209410 A1 8/2010 Schoef et al.
2010/0240619 A1 9/2010 Gregory et al.
2010/0260735 A1 10/2010 Bais et al.
2011/0212835 A1 9/2011 Bais et al.
2012/0076765 A1 3/2012 Schisler et al.
2012/0094834 A1 4/2012 Frank et al.
(Continued)

FOREIGN PATENT DOCUMENTS

AU 611315 B2 6/1991
AU 2013326645 A1 4/2014
(Continued)

OTHER PUBLICATIONS

Yuichi Matsuzaki et al, Discovery of metyltetraprole: Identification of tetrazolinone pharmacophore to overcome QoI resistance, Bioorganic & Medicinal Chemistry 28 (2020) 115211 (Year: 2020).*
Final Office Action, issued in co-pending U.S. Appl. No. 14/777,850, dated Apr. 15, 2019.
"Broadband," (Aug. 9, 2012), retrieved from Internet Jan. 29, 2014, url: http://beckerunderwood.com/media/?products/resources/brouadband_instructions_B4D27D46613D6.pdf.
Afon'kin, A.A. et al. "Synthesis of Some Electron-Rich Aryl(hetaryl)oxarines under Phase-Transfer and Homogenous Conditions," Russian Journal of Organic Chemistry, 2008, p. 1776-1779, vol. 44, No. 12.
(Continued)

*Primary Examiner* — Jason Deck
(74) *Attorney, Agent, or Firm* — Marshall, Gerstein & Borun LLP

(57) ABSTRACT

The present invention relates to the use of use of a tetrazolinones for combating phytopathogenic fungi on soybean, such fungi containing a G143A mutation in the mitochondrial cytochrome b gene conferring resistance to Qo inhibitors.

7 Claims, No Drawings

(56) References Cited

U.S. PATENT DOCUMENTS

| | | | | |
|---|---|---|---|---|
| 2012/0149571 | A1 | 6/2012 | Kloepper et al. | |
| 2013/0137658 | A1 | 5/2013 | Matsuzaki | |
| 2014/0005047 | A1 | 1/2014 | Hungenberg et al. | |
| 2014/0012855 | A1 | 1/2014 | Firat et al. | |
| 2014/0112899 | A1 | 4/2014 | Jeschke et al. | |
| 2014/0127322 | A1 | 5/2014 | Oberholzer et al. | |
| 2014/0323305 | A1 * | 10/2014 | Rheinheimer | A01N 37/50 504/206 |
| 2015/0051171 | A1 | 2/2015 | Yoshimoto et al. | |
| 2015/0250173 | A1 | 9/2015 | Körber et al. | |
| 2015/0299146 | A1 | 10/2015 | Hasegawa et al. | |
| 2016/0278384 | A1 | 9/2016 | Jabs et al. | |

FOREIGN PATENT DOCUMENTS

| | | | | |
|---|---|---|---|---|
| CA | 1086734 | A | 9/1980 | |
| CA | 1100976 | A | 5/1981 | |
| CA | 1187084 | A | 5/1985 | |
| CA | 1209152 | A | 8/1986 | |
| CA | 1210404 | A | 8/1986 | |
| CL | 2012002419 | A1 | 7/2014 | |
| CL | 2015002622 | A1 | 4/2016 | |
| CN | 1086664 | A | 5/1994 | |
| CN | 1335854 | A | 2/2002 | |
| CN | 1456054 | A | 11/2003 | |
| CN | 1475560 | A | 2/2004 | |
| CN | 1907024 | A | 2/2007 | |
| CN | 101028009 | A | 9/2007 | |
| CN | 101225074 | A | 7/2008 | |
| CN | 101697736 | A | 4/2010 | |
| CN | 101697737 | A | 4/2010 | |
| CN | 101917856 | A | 12/2010 | |
| CS | 247200 | B2 | 12/1986 | |
| DE | 2325878 | A1 | 12/1974 | |
| DE | 3801233 | A1 | 8/1988 | |
| DE | 3733755 | A1 | 4/1989 | |
| DE | 4003180 | A1 | 8/1991 | |
| DE | 102009009240 | A1 | 8/2010 | |
| EP | 0000017 | B1 | 9/1981 | |
| EP | 0077479 | A2 | 4/1983 | |
| EP | 0114567 | B1 | 9/1988 | |
| EP | 0113640 | B1 | 5/1990 | |
| EP | 0275955 | B1 | 7/1990 | |
| EP | 0126430 | B1 | 8/1991 | |
| EP | 0470466 | A2 | 2/1992 | |
| EP | 354183 | B1 | 1/1993 | |
| EP | 0440950 | B1 | 11/1993 | |
| EP | 1700919 | A1 | 9/2006 | |
| EP | 1431275 | B1 | 4/2010 | |
| EP | 2649879 | A1 | 10/2013 | |
| EP | 1469122 | B1 | 2/2014 | |
| EP | 2815649 | A1 | 12/2014 | |
| EP | 2835052 | A1 | 2/2015 | |
| EP | 2865265 | A1 | 4/2015 | |
| EP | 2910126 | A1 | 8/2015 | |
| EP | 2962568 | A1 | 1/2016 | |
| FR | 2491924 | A1 | 4/1982 | |
| GB | 2064520 | A1 | 6/1981 | |
| GB | 2132195 | A1 | 7/1984 | |
| GB | 2143815 | A1 | 2/1985 | |
| GB | 2481118 | A | 12/2011 | |
| JP | 59-222434 | A | 12/1984 | |
| JP | 2-83304 | A | 3/1990 | |
| NZ | 230176 | A | 1/1992 | |
| RU | 2478290 | C2 | 4/2013 | |
| WO | 9401546 | A1 | 1/1994 | |
| WO | 9410846 | A1 | 5/1994 | |
| WO | 9619112 | A1 | 6/1996 | |
| WO | 96041804 | A1 | 12/1996 | |
| WO | 00029426 | A1 | 5/2000 | |
| WO | 02060250 | A2 | 8/2002 | |
| WO | 02085891 | A1 | 10/2002 | |
| WO | 02091824 | A2 | 11/2002 | |
| WO | 03016303 | A1 | 2/2003 | |
| WO | 03064572 | A1 | 8/2003 | |
| WO | 05123689 | A1 | 12/2005 | |
| WO | 05123690 | A1 | 12/2005 | |
| WO | 06015866 | A1 | 2/2006 | |
| WO | 06016708 | A1 | 2/2006 | |
| WO | 06037632 | A1 | 4/2006 | |
| WO | 06087373 | A1 | 8/2006 | |
| WO | 06109933 | A1 | 10/2006 | |
| WO | 06119876 | A1 | 11/2006 | |
| WO | 07031308 | A2 | 3/2007 | |
| WO | 07072999 | A1 | 6/2007 | |
| WO | 07129454 | A1 | 11/2007 | |
| WO | 08013622 | A2 | 1/2008 | |
| WO | 08082198 | A1 | 7/2008 | |
| WO | 09037242 | A2 | 3/2009 | |
| WO | 09090181 | A2 | 7/2009 | |
| WO | 09094442 | A2 | 7/2009 | |
| WO | 10043319 | A1 | 4/2010 | |
| WO | 10109436 | A1 | 9/2010 | |
| WO | 10128003 | A2 | 11/2010 | |
| WO | 10139271 | A1 | 12/2010 | |
| WO | 10139656 | A2 | 12/2010 | |
| WO | 10146114 | A1 | 12/2010 | |
| WO | 11081174 | A1 | 7/2011 | |
| WO | 11099804 | A2 | 8/2011 | |
| WO | 11109395 | A2 | 9/2011 | |
| WO | 11114280 | A2 | 9/2011 | |
| WO | 11117272 | A2 | 9/2011 | |
| WO | 11147953 | A1 | 12/2011 | |
| WO | 11154494 | A2 | 12/2011 | |
| WO | 11162397 | A1 | 12/2011 | |
| WO | 12020772 | A1 | 2/2012 | |
| WO | 12023143 | A1 | 2/2012 | |
| WO | 12037782 | A1 | 3/2012 | |
| WO | 12047608 | A2 | 4/2012 | |
| WO | 12072696 | A1 | 6/2012 | |
| WO | 12076563 | A1 | 6/2012 | |
| WO | 12079073 | A1 | 6/2012 | |
| WO | 12080415 | A1 | 6/2012 | |
| WO | 12163945 | A1 | 12/2012 | |
| WO | 13007767 | A1 | 1/2013 | |
| WO | 13010862 | A1 | 1/2013 | |
| WO | 13010885 | A1 | 1/2013 | |
| WO | 13010894 | A1 | 1/2013 | |
| WO | 13024075 | A1 | 2/2013 | |
| WO | 13024076 | A1 | 2/2013 | |
| WO | 13024077 | A1 | 2/2013 | |
| WO | 13024080 | A1 | 2/2013 | |
| WO | 13024081 | A1 | 2/2013 | |
| WO | 13024082 | A1 | 2/2013 | |
| WO | 13050302 | A1 | 4/2013 | |
| WO | 13092224 | A1 | 6/2013 | |
| WO | 13116251 | A2 | 8/2013 | |
| WO | 13162072 | A1 | 10/2013 | |
| WO | 13162077 | A1 | 10/2013 | |
| WO | 13162716 | A2 | 10/2013 | |
| WO | WO-2013162072 | A1 * | 10/2013 | C07D 403/12 |
| WO | 14007663 | A1 | 1/2014 | |
| WO | 14013223 | A1 | 1/2014 | |
| WO | 14029697 | A1 | 2/2014 | |
| WO | 14051161 | A1 | 4/2014 | |
| WO | 14051165 | A1 | 4/2014 | |
| WO | 14053398 | A1 | 4/2014 | |
| WO | 14060177 | A1 | 4/2014 | |
| WO | 14076663 | A1 | 5/2014 | |
| WO | 14079719 | A1 | 5/2014 | |
| WO | 14079724 | A1 | 5/2014 | |
| WO | 14079728 | A1 | 5/2014 | |
| WO | 14079730 | A1 | 5/2014 | |
| WO | 14079752 | A1 | 5/2014 | |
| WO | 14079754 | A1 | 5/2014 | |
| WO | 14079764 | A1 | 5/2014 | |
| WO | 14079766 | A1 | 5/2014 | |
| WO | 14079769 | A1 | 5/2014 | |
| WO | 14079770 | A1 | 5/2014 | |
| WO | 14079771 | A1 | 5/2014 | |
| WO | 14079772 | A1 | 5/2014 | |
| WO | 14079773 | A1 | 5/2014 | |
| WO | 14079774 | A1 | 5/2014 | |

(56) References Cited

FOREIGN PATENT DOCUMENTS

| | | | |
|---|---|---|---|
| WO | 14079804 | A1 | 5/2014 |
| WO | 14079813 | A1 | 5/2014 |
| WO | 14079814 | A1 | 5/2014 |
| WO | 14079841 | A1 | 5/2014 |
| WO | 14084223 | A1 | 6/2014 |
| WO | 14086848 | A1 | 6/2014 |
| WO | 14086850 | A1 | 6/2014 |
| WO | 14086851 | A1 | 6/2014 |
| WO | 14086853 | A1 | 6/2014 |
| WO | 14086854 | A1 | 6/2014 |
| WO | 14086856 | A1 | 6/2014 |
| WO | 14095932 | A1 | 6/2014 |
| WO | 14095994 | A1 | 6/2014 |
| WO | 14147528 | A1 | 9/2014 |
| WO | 14147534 | A1 | 9/2014 |
| WO | 14191271 | A1 | 12/2014 |
| WO | 14202421 | A1 | 12/2014 |
| WO | 15003908 | A1 | 1/2015 |
| WO | 15012243 | A1 | 1/2015 |
| WO | 15012244 | A1 | 1/2015 |
| WO | 15012245 | A1 | 1/2015 |
| WO | 15038503 | A1 | 3/2015 |
| WO | 15051171 | A1 | 4/2015 |
| WO | 15113860 | A1 | 8/2015 |
| WO | 15135701 | A1 | 9/2015 |
| WO | 15141867 | A1 | 9/2015 |
| WO | 15169711 | A1 | 11/2015 |
| WO | 15177021 | A1 | 11/2015 |
| WO | 15180983 | A1 | 12/2015 |
| WO | 15180985 | A1 | 12/2015 |
| WO | 15180987 | A1 | 12/2015 |
| WO | 15180999 | A1 | 12/2015 |
| WO | 15181008 | A1 | 12/2015 |
| WO | 15181009 | A1 | 12/2015 |
| WO | 15181035 | A1 | 12/2015 |
| WO | 15190316 | A1 | 12/2015 |
| WO | 15197393 | A1 | 12/2015 |
| WO | 16008740 | A1 | 1/2016 |
| WO | 16071164 | A1 | 5/2016 |
| WO | 16071167 | A1 | 5/2016 |
| WO | 16071168 | A1 | 5/2016 |
| WO | 16071246 | A1 | 5/2016 |
| WO | 16078995 | A1 | 5/2016 |
| WO | 16091675 | A1 | 6/2016 |
| WO | 16174042 | A1 | 11/2016 |
| WO | 17144231 | A1 | 8/2017 |
| WO | 17153200 | A1 | 9/2017 |
| WO | 17157910 | A1 | 9/2017 |
| WO | 17157915 | A1 | 9/2017 |
| WO | 17157916 | A1 | 9/2017 |
| WO | 17157920 | A1 | 9/2017 |
| WO | 17157923 | A1 | 9/2017 |

OTHER PUBLICATIONS

Akama, Tsutomu, et al. "Discovery and structure-activity study of a novel benzoxaborole anti-inflammatory agent (AN2728) for the potential topical treatment of psoriasis and atopic dermatitis," Bioorganic & Medicinal Chemistry Letters, 2009, p. 2129-2132, vol. 19.

Bartlett, D.W., "The strobilurin fungicides", Pest Management Science, 2002, pp. 649-662, vol. 58.

Bennett et al., "Survival of the Biocontrol Agents Coniothyrium minitans and Bacillus subtilis MBI 600 Introduced into Pasturised, Sterilised and Non-Sterile Soils," Soil Biology & Biochemistry, vol. 35, (2003), pp. 1565-1573.

Brandes, Bridget D., et al., "Synthesis of enantiopure 3-chlorostyrene oxide via an asymmetric epoxidation-hydrolytic kinetic resolution sequence," Tetrahedron; Asymmetry, 1997, p. 3927-3933, vol. 8, No. 23.

Echeveeri-Molina et al., "Toxicity of Synthetic and Biological Insecticides against Adults of the Eucalyptus Snout-Beetle Gonipterus scutellatus Gyllenhal (Coleoptera: Curculionidae)," Journal of Pest Science, vol. 83, (2010), pp. 297-305.

Enebak, S.A, et al., "Evidence for Induced Systemic Protection to Fusiform Rust in Loblolly Pine by Plant Growth-Promoting Rhizobacteria", The American Phytopathological Society, Plant Disease/Mar. 2000, vol. 84, No. 3, pp. 306-308.

Facts on Friday Bulletin, Cotton Seed Distributors Extension and Development Team, Jul. 23, 2010 (one page).

Farenhorst, Marit, et al., "Synergy in Efficacy of Fungal Entomopathogens and Permethrin against West African Insecticide-Resistant Anopheles gambiae Mosquitoes", PloS One, Aug. 2010, vol. 5, Issue 8, 10p.

Final Office Action, issued in co-pending U.S. Appl. No. 14/443,844, dated Jun. 23, 2017.

Final Office Action, issued in co-pending U.S. Appl. No. 14/443,206, dated Dec. 12, 2017.

Final Office Action, issued in co-pending U.S. Appl. No. 14/443,844, dated Jul. 11, 2018.

Final Office Action, issued in co-pending Application No. 14/777,845, dated Nov. 22, 2017.

Final Office Action, issued in co-pending Application No. 14/777,850, dated Mar. 30, 2018.

Final Office Action, issued in co-pending Application No. 14/777,845, dated Nov. 13, 2018.

Final Office Action, issued in co-pending U.S. Appl. No. 15/313,229, dated Jun. 14, 2018.

Final Office Action, issued in co-pending U.S. Appl. No. 14/443,206, dated Mar. 4, 2019.

Forrester, Julie, et al. "Generation of trimethylsulfonium cation from dimethyl sulfoxide and dimethyl sulfate: implication s for the synthesis of epoxides from aldehydes and ketones," J. Chem. Soc. Perkin Trans. 1, 1995, pp. 2289-2291, vol. 1995.

Koch et al., "64. Biosynthesis of cis-Jasmone: A Pathway for the Inactivation and the Disposal of the Plant Stress Hormone Jasmonic Acid to the Gas Phase?" Helvetica Chimica Acta, vol. 80, (1997), pp. 838-850.

Kuzenkov, A.V., "Synthesis of substituted 2-azoloyl-1-pyridylethan-1-ols," Chemistry of hererocyclic compounds, 2003, p. 1492-1495 vol. 39, No. 11.

Leisso et al., "The Influence of Biological and Fungicidal Seed Treatments on Chickpea (*Cicer arietinum*) Damping Off," Can J Plant Pathol., vol. 31, (2009), pp. 38-46.

Lima, Lidia Moreira et al., "Bioisosterism: A useful strategy for molecular Modification and drug design," Current Medicinal Chemistry, 2005, p. 23-49, vol. 12.

McKnight and Rossall, "Root Colonization of Cotton Seedlings by Bacillus subtilis MBI 600," 2nd International Workshop on Plant Growth-Promoting Rhizobacteria, (1991), pp. 365-369.

Mosset, Paul et al. "Trimethylsulfonium Methylsulfate, a simple and efficient epoxidizing agent," Synthetic Communications, 1985, p. 749-757, vol. 15, No. 8.

Office Action dated Apr. 3, 2017 for co-pending U.S. Appl. No. 14/777,845.

Office Action dated Feb. 6, 2018 for co-pending U.S. Appl. No. 15/313,229.

Office Action dated Jun. 23, 2017, from U.S. Appl. No. 14/443,844, filed May 19, 2015.

Office Action, issued in co-pending U.S. Appl. No. 14/443,206, dated Apr. 5, 2017.

Office Action, issued in co-pending U.S. Appl. No. 14/443,206, dated May 25, 2018.

Office Action, issued in co-pending U.S. Appl. No. 14/443,520, dated Oct. 14, 2016.

Office Action, issued in co-pending U.S. Appl. No. 14/443,523, dated Sep. 19, 2016.

Office Action, issued in co-pending U.S. Appl. No. 14/443,844, dated Feb. 14, 2017.

Office Action, issued in co-pending U.S. Appl. No. 14/777,845, dated Nov. 22, 2017.

Office Action, issued in co-pending U.S. Appl. No. 14/777,845, dated Apr. 3, 2017.

Office Action, issued in co-pending U.S. Appl. No. 14/777,845, dated May 29, 2018.

Office Action, issued in co-pending U.S. Appl. No. 14/777,850, dated Mar. 24, 2017.

(56) References Cited

OTHER PUBLICATIONS

Office Action, issued in co-pending U.S. Appl. No. 14/777,850, dated Oct. 1, 2018.
Office Action, issued in corresponding CL Application No. 15/8002684, dated Mar. 27, 2017.
Office Action, issued in corresponding CN Application No. 201380071087.5, dated Apr. 26, 2017.
Office Action, issued in corresponding CN Application No. 201480016731.3, dated Apr. 28, 2017.
Office Action, issued in corresponding UA Application No. 1506049, dated Feb. 14, 2017.
Schisler et al., "Formulation of *Bacillus* spp. for Biological Control of Plant Diseases," Journal of Phytopathology, vol. 94, (2004), pp. 1267-1271.
Schmidt et al., "Influence of Soil Temperature and Matric Potential on Sugar Beet Seedling Colonization and Suppression of Pythium Damping-Off by the Antagonistic Bacteria Pseudomonas fluorescens and Bacillus subtilis," Phytopathology, vol. 94, No. 4, (2004), pp. 351-363.
Singh et al., "DuPont CyazypyrTM (DPX-HGW86, cyantraniliprole): A Cross-Spectrum Insecticide for Control of Major Pests of Rice," Abstract of Conference Paper, Entomological Society of America Annual, (2011), retrieved from the Internet on Feb. 9, 2017: https://www.researchgate.net/publication/267528306_DuPont_Cyazypyr_DPX-HGW86_c.
Stamina Supplemental label, BASF Corp, Research Triangle Park, NC, 2011, pp. 1-3.
Wang, "Research Progress and Prospect of Bacillus Subtilis," Journal of the Graduates, Sun Yat-Sen University (Natural Sciences, Medicine), 2012, vol. 33, Issue 3, pp. 14-22.
Wright et al., "Application of Beneficial Microorganisms to Seeds During Drum Priming," Biocontrol Science and Technology, (2003), pp. 599-614.
International Search Report, issued in PCT/EP2017/055956, dated Apr. 10, 2017.
International Preliminary Report on Patentability, issued in PCT/EP2017/055956, dated Sep. 18, 2018.
FRAC Fungicide Resistance Action Committee: "List of Pathogens with Field Resistance towards Qol Fungicides," [on-line], retrieved from http://www.frac.info/docs/default-source/qoi-quick-references/species-with-qo-resistance-%28updated-2012%29.pdf?sfvrsn=4 [retrieved May 2, 2016].
Soares et al., "More Cercospora Species Infect Soybeans Across the Americas than Meets the Eye," PLOS ONE, vol. 10, No. 8, (2015), p. e0133495.
Kataoka et al., "Mechanism of Action and Selectivity of a Novel Fungicide, Pyribencarb," Journal of Pesticide Science, vol. 35, No. 2, (2010), pp. 99-106.
Office Action, issued in co-pending U.S. Appl. No. 15/524,064, dated Apr. 2, 2019.
Yu et al., "Synthesis and Fungicidal Evaluation of 2-arylphenyl ether-3-(1H-1,2,4-triazol-1-yl)propan-2-of Derivatives," Journal of Agricultural and Food Chemistry, vol. 57, No. 11, (2009), pp. 4854-4860.
Zhang, "Evaluation of Microbial Products for Management of Powdery Mildew on Summer Squash and Cantaloupe in Florida," Plant Disease, (2011), pp. 461-468.
Zhou, X. G., et al., "Field evaluation of a beneficial Bacillus strain for biocontrol of sheath blight in rice", Phytopathology, 2011, vol. 101, S204.
Zitter et al., "Control of Early Blight of Tomato with Genetic Resistance and Conventional and Biological Sprays," Proc. 1st IS on Tomato Diseases, Acta Hort, vol. 695, (2005), pp. 181-190.
Standish, et al., "Occurrence of Qol Fungicide Resistance in Cercospora sojina from Mississippi Soybean", Plant Disease, vol. 99, Issue 10, Oct. 2015, pp. 1347-1352.
Zeng, et al., "Characterization of Quinone Outside Inhibitor Fungicide Resistance in Cercospora sojina and Development of Diagnostic Tools for its Identification", Plant Disease, vol. 99, Issue 4, 2015, pp. 544-550.
European Search Report for EP Patent Application No. 16160603.3, dated Sep. 5, 2016.
Jeanmart, et al., "Synthetic Approaches to the 2010-2014 New Agrochemicals", Bioorganic & Medicinal Chemistry, vol. 24, Issue 3, 2016, pp. 317-341.
Tedford et al., Fundamental Aspects for the Development of Resistance to Fungicides, (2007), [online] retrieved from: https://www.plantmanagementnetwork.org/infocenter/topic/soybeanrust/2007/presentations/Tedford.pdf [retrieved Oct. 8, 2018].
Rallos, Characterizing Resistance of the Grapevine Powdery Mildew Erysiphe necator to Fungicides Belonging to Quinone Outside Inhibitors and Demethylation Inhibitors, (2012) [online] retrieved from: https://vtechworks.lib.vt.edu/bitstream/handle/10919/49594/Rallos_LE-D-2013.pdf?sequence=1 [retrieved Oct. 8, 2018].
Dehne et al., Modern Fungicides and Antifungal Compounds V, Proceedings of the 15th International Reinhardsbrunn Symposium on Modem Fungicides and Antifungal Compounds, (2007), [online] retrieved from: http://dpg.phytomedizin.org/fileadmin/daten/04_Verlag/02_SP/05_Reinhard/0294-sp-2008-Reinh-4.pdf.
Kianianmomeni et al., Validation of a Real-Time PCR for the Quantitative Estimation of a G143A Mutation in the Cytochromebc1 Gene of *Pyrenophora teres*, Pest Management Science, vol. 63, No. 3, (2007), pp. 219-224.
Fraaije, et al., "Role of Ascospores in Further Spread of Qol-Resistant Cytochrome b Alleles (G143A) in Field Populations of Mycosphaerella graminicola", Phytopathology, vol. 95, Issue 8, Aug. 2005, pp. 933-941.
John Lucas, "Resistance to Qol fungicides: implications for cereal disease management in Europe", Pesticide Outlook, vol. 14, Issue 6, 2003, pp. 268-270.
Pasche, et al., "Prevalence, competitive fitness and impact of the F129L mutation in Alternaria solani from the United States", Crop Protection, vol. 27, Issues 3-5, Mar.-May 2008, pp. 427-435.
Semar, et al., "Field efficacy of pyraclostrobin against populations of Pyrenophora teres containing the F129L mutation in the cytochrome b gene", Journal of Plant Diseases and Protection, vol. 114, Issue 3, Jun. 2007, pp. 117-119.
Sierotzki, et al., "Cytochrome b gene sequence and structure of Pyrenophora teres and P. triticirepentis and implications for Qol resistance", Pest Management Science, vol. 63, Issue 3, Mar. 2007, pp. 225-233.
Sierotzki, et al., "Mode of resistance to respiration inhibitors at the cytochrome bc1 enzyme complex of Mycosphaerella fijiensis field isolates", Pest Management Science, vol. 56, Issue 10, 2000, pp. 833-841.
Kuck et al., "Chapter 12. FRAC Mode of Action Classification and Resistance Risk of Fungicides," Modem Crop Protection Compounds, (2007), pp. 415-432.
Office Action, issued in co-pending U.S. Appl. No. 16/083,898, dated Sep. 27, 2019.

* cited by examiner

USE OF TETRAZOLINONES FOR COMBATING RESISTANT PHYTOPATHOGENIC FUNGI ON SOYBEAN

CROSS-REFERENCE TO RELATED APPLICATIONS

This application is a National Stage application of International Application No. PCT/EP2017/055956, filed Mar. 14, 2017. This application also claims priority under 35 U.S.C. § 119 to European Patent Application No. 16160603.3, filed Mar. 16, 2016.

The present invention relates to the use of use of 1-[2-[[1-(4-chlorophenyl)pyrazol-3-yl]oxymethyl]-3-methyl-phenyl]-4-methyl-tetrazol-5-one (herein also referred to as compound I) for combating phytopathogenic fungi on soybean, such fungi containing a G143A mutation in the mitochondrial cytochrome b gene conferring resistance to Qo inhibitors.

Qo inhibitor fungicides, often referred to as strobilurin-type fungicides (Sauter 2007: Chapter 13.2. Strobilurins and other complex III inhibitors. In: Krämer, W.; Schirmer. U. (Ed.)—Modern Crop Protection Compounds. Volume 2. Wiley-VCH Verlag 457-495), are conventionally used to control a number of fungal pathogens in crops. Qo inhibitors typically work by inhibiting respiration by binding to a ubihydroquinone oxidation center of a cytochrome $bc_1$ complex (electron transport complex III) in mitochondria. Said oxidation center is located on the outer side of the inner mitochrondrial membrane. A prime example of the use of Qo inhibitors includes the use of, for example, strobilurins on soybean for the control of *Cercospora sojina*, which is the cause of frogeye leaf spot on soybeans. Unfortunately, widespread use of such Qo inhibitors has resulted in the selection of mutant pathogens which are resistant to such Qo inhibitors (Zeng et al., PLANT DISEASE 99(4), 544-550 (2015); Standish et al., PLANT DISEASE 99(10), 1347-1352 (2015). Resistance to Qo inhibitors has been detected in several phytopathogenic fungi. In some pathogens, the major part of resistance to Qo inhibitors in agricultural uses has been attributed to pathogens containing a single amino acid residue substitution G143A in the cytochrome b gene for their cytochrome $bc_1$ complex, the target protein of Qo inhibitors (see, for example Lucas, Pestic Outlook 14(6), 268-70 (2003); and Fraaije et al., Phytopathol 95(8), 933-41 (2005).

In soybean, the following pathogens show increasing resistance towards Qo inhibitors due to their G143A mutation:

*Cercospora sojina* (frogeye leaf spot) and *Corynespora cassiicola* (target spot).

Thus, new methods and compositions are desirable for controlling these pathogen induced diseases in crops comprising plants subjected to pathogens that are resistant to Qo inhibitors. Furthermore, in many cases, in particular at low application rates, the fungicidal activity of the known fungicidal strobilurin analogue compounds is unsatisfactory, especially in case that a high proportion of the fungal pathogens contain a mutation in the mitochondrial cytochrome b gene conferring resistance to Qo inhibitors. Based on this, it was also an object of the present invention to provide compounds having improved activity and/or a broader activity spectrum against such resistant phytopathogenic harmful fungi on soybean.

"Qo inhibitor," as used herein, includes any substance that is capable of diminishing and/or inhibiting respiration by binding to an ubihydroquinone oxidation center of a cytochrome $bc_1$ complex in mitochondria. The oxidation center is typically located on the outer side of the inner mitochrondrial membrane.

From WO2013/092224, the use of Qo inhibitors is known for combating phytopathogenic fungi that are resistant to Qo inhibitors is generally known. However, neither *Cercospora sojina* (frogeye leaf spot) and *Corynespora cassiicola* (target spot) as resistant pathogen nor the specific compound of formula I are not explicitly disclosed therein. Thus, there is a constant need to find further compounds with even improved action against fungi that are resistant to Qo inhibitors on top of those disclosed in WO2013/092224.

The compounds I have surprisingly high action against *Cercospora sojina* (frogeye leaf spot) and *Corynespora cassiicola* (target spot) on soybean.

Thus, the present invention relates to the use of 1-[2-[[1-(4-chlorophenyl)pyrazol-3-yl]oxymethyl]-3-methyl-phenyl]-4-methyl-tetrazol-5-one (herein also referred to as compound I) for combating phytopathogenic fungi containing a mutation in the mitochondrial cytochrome b gene conferring resistance to Qo inhibitors on soybean, wherein the mutation is G143A.

The present invention also relates to the use of a mixture comprising compound I in combination with a second compound II, wherein compound II is selected from 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, prothioconazole, difenoconazole, propiconazole, tetraconazole, tebucoanzole, mancozeb, chlorothalonil, fluxapyroxad, bixafen, benzovindiflupyr, pydiflumetofen, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, penthiopyrad, isopyrazam, pyraclostrobin, (Z,2E)-5-[1-(2,4-dichlorophenyl)pyrazol-3-yl]¬oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, trifloxystrobin, picoxystrobin, azoxystrobin, mandestrobin, metominostrobin and fenpropimorph.

The present invention also relates to the use of a mixture comprising compound I in combination with two compounds II, wherein compound II is defined above.

The fungi on soybean containing a G143A mutation in the mitochondrial cytochrome h gene conferring resistance to Qo inhibitors are hereinafter referred to as "resistant fungi". Resistant fungi on soybean in the course of the use of the present invention, wherein the mutation is G143A are *Cercospora sojina* (frogeye leaf spot) and *Corynespora cassiicola* (target spot).

Thus, in a preferred embodiment, the present invention relates to the use of 1-[2-[[1-(4-chlorophenyl)pyrazol-3-yl]oxymethyl]-3-methyl-phenyl]-4-methyl-tetrazol-5-one for combating resistant fungi on soybean, wherein Y is Y1 and the resistant fungi is *Cercospora sojina*

In a further preferred embodiment, the present invention relates to the use of a of 1-[2-[[1-(4-chlorophenyl)pyrazol-3-yl]oxymethyl]-3-methyl-phenyl]-4-methyl-tetrazol-5-one for combating resistant fungi on soybean, wherein Y is Y1 and the resistant fungi is *Corynespora cassiicola.*

The present invention also relates to the use of a mixture comprising compound I in combination with a second compound II, wherein compound II is selected from 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, prothioconazole, difenoconazole, propiconazole, tetraconazole, tebucoanzole, mancozeb, chlorothalonil, fluxapyroxad, bixafen, benzovindiflupyr, pydiflumetofen, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethyindan-4-yl)pyrazole-4-carboxamide, 1,3,5-trimethyl-N-(1,1,3-trimethylindan-4-yl)pyrazole-4-carboxamide, penthiopyrad, isopyrazam, pyraclostrobin, (Z,2E)-5-[1-(2,4-dichlorophenyl)pyrazol-3-yl]¬oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, trifloxystrobin, picoxystrobin, azoxystrobin, mandestrobin, metominostrobin and fenpropimorph for combating *Cercospora sojina* and *Corynespora cassiicola* on soybean.

In a further preferred embodiment, the present invention relates to the use of any of the mixtures of compound I and compound II as defined above for combating resistant fungi on soybean, wherein the resistant fungi is *Corynespora cassiicola.*

In a further preferred embodiment, the present invention relates to the use of any of the mixtures of compound I and compound II as defined above for combating resistant fungi on soybean, wherein the resistant fungi is *Cercospora sojina.*

Thus, the present invention relates to the use of any of the mixtures M-1 to M-31 as defined in Table 1 for combating resistant fungi on soybean, and the resistant fungi is *Corynespora cassiicola.*

TABLE 1

"I" is compound I, "II" is compound II"

| No | I | II |
|---|---|---|
| M-1 | I | 2-[4-(4-chlorophenoxy)-2-(trifluoromethyl)phenyl]-1-(1,2,4-triazol-1-yl)propan-2-ol |
| M-2 | I | 2-[4-(4-chlorophenoxy)-2-(trifluoromethyl)phenyl]-3-methyl-1-(1,2,4-triazol-1-yl)butan-2-ol |
| M-3 | I | 1-[4-(4-chlorophenoxy)-2-(trifluoromethyl)phenyl]-1-cyclopropyl-2-(1,2,4-triazol-1-yl)ethanol |
| M-4 | I | fluxapyroxad |
| M-5 | I | pyraclostrobin |
| M-6 | I | (Z,2E)-5-[1-(2,4-dichlorophenyl)pyrazol-3-yl]¬oxy-2-methoxyimino-N,3-dimethyl-pent-3-enamide |
| M-7 | I | (Z,2E)-5-[1-(4-chlorophenyl)pyrazol-3-yl]oxy-2-methoxyimino-N,3-dimethyl-pent-3-enamide |
| M-8 | I | fenpropimorph |
| M-9 | I | prothioconazole |
| M-10 | I | difenoconazole |
| M-11 | I | propiconazole |
| M-12 | I | tetraconazole |
| M-13 | I | tebucoanzole |
| M-14 | I | mancozeb |
| M-15 | I | chlorothalonil |
| M-16 | I | bixafen |
| M-17 | I | benzovindiflupyr |
| M-18 | I | pydiflumetofen |
| M-19 | I | 3-(difluoromethyl)-1-methyl-N-(1,1,3-trimethylindan-4-yl)pyrazole-4-carboxamide; |
| M-20 | I | 3-(trifluoromethyl)-1-methyl-N-(1,1,3-trimethylindan-4-yl)pyrazole-4-carboxamide; |
| M-21 | I | 1,3-dimethyl-N-(1,1,3-trimethylindan-4-yl)pyrazole-4-carboxamide; |
| M-22 | I | 3-(trifluoromethyl)-1,5-dimethyl-N-(1,1,3-trimethylindan-4-yl)pyrazole-4-carboxamide; |
| M-23 | I | 3-(difluoromethyl)-1,5-dimethyl-N-(1,1,3-trimethylindan-4-yl)pyrazole-4-carboxamide; |
| M-24 | I | 1,3,5-trimethyl-N-(1,1,3-trimethylindan-4-yl)pyrazole-4-carboxamide |
| M-25 | I | penthiopyrad |
| M-26 | I | isopyrazam |
| M-27 | I | trifloxystrobin |
| M-28 | I | picoxystrobin |
| M-29 | I | azoxystrobin |
| M-30 | I | mandestrobin |
| M-31 | I | metominostrobin |

Thus, the present invention relates to the use of any of the mixtures M-1 to M-31 as defined in Table 1 for combating resistant fungi on soybean, and the resistant fungi is *Cercospora sojina.*

In a more preferred embodiment, the present invention relates to the use of any of the mixtures of compound I and compound II for combating resistant fungi on soybean, wherein compound II is selected from the group consisting of 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, fluxapyroxad, pyraclostrobin, (Z,2E)-5-[1-(2,4-dichlorophenyl)pyrazol-3-yl]¬oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide and fenpropimorph, wherein the resistant fungi is *Corynespora cassiicola.*

In a most preferred embodiment, the present invention relates to the use of any of the mixtures of compound I and compound II for combating resistant fungi on soybean, wherein compound II is selected from the group consisting of 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, prothioconazole, fluxapyroxad, metrafenone, pyraclostrobin and azoxystrobin, wherein the resistant fungi is *Cercospora sojina.*

Thus, the present invention relates to the use of any of the mixtures MB-1 to MB-8 as defined in Table 2 for combating resistant fungi on soybean, and the resistant fungi is *Corynespora cassiicola.*

TABLE 2

| "I" is compound I, "II" is compound II" | | |
|---|---|---|
| No | I | II |
| MB-1 | I | 2-[4-(4-chlorophenoxy)-2-(trifluoromethyl)phenyl]-1-(1,2,4-triazol-1-yl)propan-2-ol |
| MB-2 | I | 2-[4-(4-chlorophenoxy)-2-(trifluoromethyl)phenyl]-3-methyl-1-(1,2,4-triazol-1-yl)butan-2-ol |
| MB-3 | I | 1-[4-(4-chlorophenoxy)-2-(trifluoromethyl)phenyl]-1-cyclopropyl-2-(1,2,4-triazol-1-yl)ethanol |
| MB-4 | I | fluxapyroxad |
| MB-5 | I | pyradostrobin |
| MB-6 | I | (Z,2E)-5-[1-(2,4-dichlorophenyl)pyrazol-3-yl]¬oxy-2-methoxyimino-N,3-dimethyl-pent-3-enamide |
| MB-7 | I | (Z,2E)-5-[1-(4-chlorophenyl)pyrazol-3-yl]oxy-2-methoxyimino-N,3-dimethyl-pent-3-enamide |
| MB-8 | I | fenpropimorph |

Thus, the present invention relates to the use of any of the mixtures MB-1 to MB-48 as defined in Table 2 for combating resistant fungi on soybean, wherein the resistant fungi is *Cercospora sojina.*

The present invention also relates to the use of a mixture comprising compound I in combination with a two compounds II selected from the group consisting of 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, prothioconazole, difenoconazole, propiconazole, tetraconazole, tebucoanzole, mancozeb, chlorothalonil, fluxapyroxad, bixafen, benzovindiflupyr, pydiflumetofen, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, penthiopyrad, isopyrazam, pyraclostrobin, (Z,2E)-5-[1-(2,4-dichlorophenyl)pyrazol-3-yl]¬oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, trifloxystrobin, picoxystrobin, azoxystrobin, mandestrobin, metominostrobin and fenpropimorph for combating resistant fungi on soybean.

Thus, the present invention relates to the use of any of the mixtures M4A-1 to M4A-109 as defined in Table 3 to combat resistant fungi on soybean, wherein the resistant fungi is *Corynespora cassiicola.*

TABLE 3

| "I" is compound I, "II" is compound II" | | |
|---|---|---|
| No | I II | II (2) |
| M3A-1 | I 2-[4-(4-chlorophenoxy)-2-(trifluoromethyl)phenyl]-1-(1,2,4-triazol-1-yl)propan-2-ol | fluxapyroxad |
| M3A-2 | I 2-[4-(4-chlorophenoxy)-2-(trifluoromethyl)phenyl]-1-(1,2,4-triazol-1-yl)propan-2-ol | bixafen |
| M3A-3 | I 2-[4-(4-chlorophenoxy)-2-(trifluoromethyl)phenyl]-1-(1,2,4-triazol-1-yl)propan-2-ol | benzovindiflupyr |
| M3A-4 | I 2-[4-(4-chlorophenoxy)-2-(trifluoromethyl)phenyl]-1-(1,2,4-triazol-1-yl)propan-2-ol | pydiflumetofen |
| M3A-5 | I 2-[4-(4-chlorophenoxy)-2-(trifluoromethyl)phenyl]-1-(1,2,4-triazol-1-yl)propan-2-ol | 3-(difluoromethyl)-1-methyl-N-(1,1,3-trimethylindan-4-yl)pyrazole-4-carboxamide; |
| M3A-6 | I 2-[4-(4-chlorophenoxy)-2-(trifluoromethyl)phenyl]-1-(1,2,4-triazol-1-yl)propan-2-ol | 3-(trifluoromethyl)-1-methyl-N-(1,1,3-trimethylindan-4-yl)pyrazole-4-carboxamide; |
| M3A-7 | I 2-[4-(4-chlorophenoxy)-2-(trifluoromethyl)phenyl]-1-(1,2,4-triazol-1-yl)propan-2-ol | 1,3-dimethyl-N-(1,1,3-trimethylindan-4-yl)pyrazole-4-carboxamide; |

TABLE 3-continued

| "I" is compound I, "II" is compound II" | | |
|---|---|---|
| No | I II | II (2) |
| M3A-8 | I 2-[4-(4-chloraphenoxy)-2-(trifluoromethyl)phenyl]-1-(1,2,4-triazol-1-yl)propan-2-ol | 3-(trifluoromethyl)-1,5-dimethyl-N-(1,1,3-trimethylindan-4-yl)pyrazole-4-carboxamide; |
| M3A-9 | I 2-[4-(4-chlorophenoxy)-2-(trifluoromethyl)phenyl]-1-(1,2,4-triazol-1-yl)propan-2-ol | 3-(difluoromethyl)-1,5-dimethyl-N-(1,1,3-trimethylindan-4-yl)pyrazole-4-carboxamide; |
| M3A-10 | I 2-[4-(4-chlorophenoxy)-2-(trifluoromethyl)phenyl]-1-(1,2,4-triazol-1-yl)propan-2-ol | 1,3,5-trimethyl-N-(1,1,3-trimethylindan-4-yl)pyrazole-4-carboxamide |
| M3A-11 | I 2-[4-(4-chlorophenoxy)-2-(trifluoromethyl)phenyl]-1-(1,2,4-triazol-1-yl)propan-2-ol | penthiopyrad |
| M3A-12 | I 2-[4-(4-chlorophenoxy)-2-(trifluoromethyl)phenyl]-1-(1,2,4-triazol-1-yl)propan-2-ol | isopyrazam |
| M3A-13 | I 2-[4-(4-chlorophenoxy)-2-(trifluoromethyl)phenyl]-1-(1,2,4-triazol-1-yl)propan-2-ol | pyraclostrobin |
| M3A-14 | I 2-[4-(4-chlorophenoxy)-2-(trifluoromethyl)phenyl]-1-(1,2,4-triazol-1-yl)propan-2-ol | (Z,2E)-5-[1-(2,4-dichlorophenyl)pyrazol-3-yl]¬oxy-2-methoxyimino-N,3-dimethyl-pent-3-enamide |
| M3A-15 | I 2-[4-(4-chlorophenoxy)-2-(trifluoromethyl)phenyl]-1-(1,2,4-triazol-1-yl)propan-2-ol | (Z,2E)-5-[1-(4-chlorophenyl)pyrazol-3-yl]oxy-2-methoxyimino-N,3-dimethyl-pent-3-enamide |
| M3A-16 | I 2-[4-(4-chlorophenoxy)-2-(trifluoromethyl)phenyl]-1-(1,2,4-triazol-1-yl)propan-2-ol | trifloxystrobin |
| M3A-17 | I 2-[4-(4-chlorophenoxy)-2-(trifluoromethyl)phenyl]-1-(1,2,4-triazol-1-yl)propan-2-ol | picoxystrobin |
| M3A-18 | I 2-[4-(4-chlorophenoxy)-2-(trifluoromethyl)phenyl]-1-(1,2,4-triazol-1-yl)propan-2-ol | azoxystrobin |
| M3A-19 | I 2-[4-(4-chlorophenoxy)-2-(trifluoromethyl)phenyl]-1-(1,2,4-triazol-1-yl)propan-2-ol | mandestrobin |
| M3A-20 | I 2-[4-(4-chlorophenoxy)-2-(trifluoromethyl)phenyl]-1-(1,2,4-triazol-1-yl)propan-2-ol | metominosirobin |
| M3A-21 | I 2-[4-(4-chlorophenoxy)-2-(trifluoromethyl)phenyl]-1-(1,2,4-triazol-1-yl)propan-2-ol | mancozeb |
| M3A-22 | I 2-[4-(4-chlorophenoxy)-2-(trifluoromethyl)phenyl]-1-(1,2,4-triazol-1-yl)propan-2-ol | chlorothalonil |
| M3A-23 | I 2-[4-(4-chlorophenoxy)-2-(trifluoromethyl)phenyl]-1-(1,2,4-triazol-1-yl)propan-2-ol | fenpropimorph |
| M3A-24 | I 2-[4-(4-chlorophenoxy)-2-(trifluoromethyl)phenyl]-3-methyl-1-(1,2,4-triazol-1-yl)butan-2-ol | fluxapyroxad |
| M3A-25 | I 2-[4-(4-chlorophenoxy)-2-(trifluoromethyl)phenyl]-3-methyl-1-(1,2,4-triazol-1-yl)butan-2-ol | bixafen |
| M3A-26 | I 2-[4-(4-chlorophenoxy)-2-(trifluoromethyl)phenyl]-3-methyl-1-(1,2,4-triazol-1-yl)butan-2-ol | benzovindiflupyr |
| M3A-27 | I 2-[4-(4-chlorophenoxy)-2-(trifluoromethyl)phenyl]-3-methyl-1-(1,2,4-triazol-1-yl)butan-2-ol | pydiflumetofen |
| M3A-28 | I 2-[4-(4-chlorophenoxy)-2-(trifluoromethyl)phenyl]-3-methyl-1-(1,2,4-triazol-1-yl)butan-2-ol | 3-(difluoromethyl)-1-methyl-N-(1,1,3-trimethylindan-4-yl)pyrazole-4-carboxamide; |
| M3A-29 | I 2-[4-(4-chlorophenoxy)-2-(trifluoromethyl)phenyl]-3-methyl-1-(1,2,4-triazol-1-yl)butan-2-ol | 3-(trifluoromethyl)-1-methyl-N-(1,1,3-trimethylindan-4-yl)pyrazole-4-carboxamide; |
| M3A-30 | I 2-[4-(4-chlorophenoxy)-2-(trifluoromethyl)phenyl]-3-methyl-1-(1,2,4-triazol-1-yl)butan-2-ol | 1,3-dimethyl-N-(1,1,3-trimethylindan-4-yl)pyrazole-4-carboxamide; |

TABLE 3-continued

| “I” is compound I, “II” is compound II” | | |
|---|---|---|
| No | I II | II (2) |
| M3A-31 | I 2-[4-(4-chlorophenoxy)-2-(trifluoromethyl)phenyl]-3-methyl-1-(1,2,4-triazol-1-yl)butan-2-ol | 3-(trifluoromethyl)-1,5-dimethyl-N-(1,1,3-trimethylindan-4-yl)pyrazole-4-carboxamide; |
| M3A-32 | I 2-[4-(4-chlorophenoxy)-2-(trifluoromethyl)phenyl]-3-methyl-1-(1,2,4-triazol-1-yl)butan-2-ol | 3-(difluoromethyl)-1,5-dimethyl-N-(1,1,3-trimethylindan-4-yl)pyrazole-4-carboxamide; |
| M3A-33 | I 2-[4-(4-chlorophenoxy)-2-(trifluoromethyl)phenyl]-3-methyl-1-(1,2,4-triazol-1-yl)butan-2-ol | 1,3,5-trimethyl-N-(1,1,3-trimethylindan-4-yl)pyrazole-4-carboxamide |
| M3A-34 | I 2-[4-(4-chlorophenoxy)-2-(trifluoromethyl)phenyl]-3-methyl-1-(1,2,4-triazol-1-yl)butan-2-ol | penthiopyrad |
| M3A-35 | I 2-[4-(4-chlorophenoxy)-2-(trifluoromethyl)phenyl]-3-methyl-1-(1,2,4-triazol-1-yl)butan-2-ol | isopyrazam |
| M3A-36 | I 2-[4-(4-chlorophenoxy)-2-(trifluoromethyl)phenyl]-3-methyl-1-(1,2,4-triazol-1-yl)butan-2-ol | pyraclostrobin |
| M3A-37 | I 2-[4-(4-chlorophenoxy)-2-(trifluoromethyl)phenyl]-3-methyl-1-(1,2,4-triazol-1-yl)butan-2-ol | (Z,2E)-5-[1-(2,4-dichlorophenyl)pyrazol-3-yl]¬oxy-2-methoxyimino-N,3-dimethyl-pent-3-enamide |
| M3A-38 | I 2-[4-(4-chlorophenoxy)-2-(trifluoromethyl)phenyl]-3-methyl-1-(1,2,4-triazol-1-yl)butan-2-ol | (Z,2E)-5-[1-(4-chlorophenyl)pyrazol-3-yl]oxy-2-methoxyimino-N,3-dimethyl-pent-3-enamide |
| M3A-39 | I 2-[4-(4-chlorophenoxy)-2-(trifluoromethyl)phenyl]-3-methyl-1-(1,2,4-triazol-1-yl)butan-2-ol | trifloxystrobin |
| M3A-40 | I 2-[4-(4-chlorophenoxy)-2-(trifluoromethyl)phenyl]-3-methyl-1-(1,2,4-triazol-1-yl)butan-2-ol | picoxystrobin |
| M3A-41 | I 2-[4-(4-chlorophenoxy)-2-(trifluoromethyl)phenyl]-3-methyl-1-(1,2,4-triazol-1-yl)butan-2-ol | azoxystrobin |
| M3A-42 | I 2-[4-(4-chlorophenoxy)-2-(trifluoromethyl)phenyl]-3-methyl-1-(1,2,4-triazol-1-yl)butan-2-ol | mandestrobin |
| M3A-43 | I 2-[4-(4-chlorophenoxy)-2-(trifluoromethyl)phenyl]-3-methyl-1-(1,2,4-triazol-1-yl)butan-2-ol | metominostrobin |
| M3A-44 | I 2-[4-(4-chlorophenoxy)-2-(trifluoromethyl)phenyl]-3-methyl-1-(1,2,4-triazol-1-yl)butan-2-ol | mancozeb |
| M3A-45 | I 2-[4-(4-chlorophenoxy)-2-(trifluoromethyl)phenyl]-3-methyl-1-(1,2,4-triazol-1-yl)butan-2-ol | chlorothalonil |
| M3A-46 | I 2-[4-(4-chlorophenoxy)-2-(trifluoromethyl)phenyl]-3-methyl-1-(1,2,4-triazol-1-yl)butan-2-ol | fenpropimorph |
| M3A-47 | I 1-[4-(4-chlorophenoxy)-2-(trifluoromethyl)phenyl]-1-cyclopropyl-2-(1,2,4-triazol-1-yl)ethanol | fluxapyroxad |
| M3A-48 | I 1-[4-(4-chlorophenoxy)-2-(trifluoromethyl)phenyl]-1-cyclopropyl-2-(1,2,4-triazol-1-yl)ethanol | bixafen |
| M3A-49 | I 1-[4-(4-chlorophenoxy)-2-(trifluoromethyl)phenyl]-1-cyclopropyl-2-(1,2,4-triazol-1-yl)ethanol | benzovindiflupyr |
| M3A-50 | I 1-[4-(4-chlorophenoxy)-2-(trifluoromethyl)phenyl]-1-cyclopropyl-2-(1,2,4-triazol-1-yl)ethanol | pydiflumetofen |
| M3A-51 | I 1-[4-(4-chlorophenoxy)-2-(trifluoromethyl)phenyl]-1-cyclopropyl-2-(1,2,4-triazol-1-yl)ethanol | 3-(difluoromethyl)-1-methyl-N-(1,1,3-trimethylindan-4-yl)pyrazole-4-carboxamide; |
| M3A-52 | I 1-[4-(4-chlorophenoxy)-2-(trifluoromethyl)phenyl]-1-cyclopropyl-2-(1,2,4-triazol-1-yl)ethanol | 3-(trifluoromethyl)-1-methyl-N-(1,1,3-trimethylindan-4-yl)pyrazole-4-carboxamide; |
| M3A-53 | I 1-[4-(4-chlorophenoxy)-2-(trifluoromethyl)phenyl]-1-cyclopropyl-2-(1,2,4-triazol-1-yl)ethanol | 1,3-dimethyl-N-(1,1,3-trimethylindan-4-yl)pyrazole-4-carboxamide; |
| M3A-54 | I 1-[4-(4-chlorophenoxy)-2-(trifluoromethyl)phenyl]-1-cyclopropyl-2- | 3-(trifluoromethyl)-1,5-dimethyl-N-(1,1,3- |

TABLE 3-continued

"I" is compound I, "II" is compound II"

| No | I II | II (2) |
|---|---|---|
| | (1,2,4-triazol-1-yl)ethanol | trimethylindan-4-yl)pyrazole-4-carboxamide; |
| M3A-55 | I 1-[4-(4-chlorophenoxy)-2-(trifluoromethyl)phenyl]-1-cyclopropyl-2-(1,2,4-triazol-1-yl)ethanol | 3-(difluoromethyl)-1,5-dimethyl-N-(1,1,3-trimethylindan-4-yl)pyrazole-4-carboxamide; |
| M3A-56 | I 1-[4-(4-chlorophenoxy)-2-(trifluoromethyl)phenyl]-1-cyclopropyl-2-(1,2,4-triazol-1-yl)ethanol | 1,3,5-trimethyl-N-(1,1,3-trimethylindan-4-yl)pyrazole-4-carboxamide |
| M3A-57 | I 1-[4-(4-chlorophenoxy)-2-(trifluoromethyl)phenyl]-1-cyclopropyl-2-(1,2,4-triazol-1-yl)ethanol | penthiopyrad |
| M3A-58 | I 1-[4-(4-chlorophenoxy)-2-(trifluoromethyl)phenyl]-1-cyclopropyl-2-(1,2,4-triazol-1-yl)ethanol | isopyrazam |
| M3A-59 | I 1-[4-(4-chlorophenoxy)-2-(trifluoromethyl)phenyl]-1-cyclopropyl-2-(1,2,4-triazol-1-yl)ethanol | pyraclostrobin |
| M3A-60 | I 1-[4-(4-chlorophenoxy)-2-(trifluoromethyl)phenyl]-1-cyclopropyl-2-(1,2,4-triazol-1-yl)ethanol | (Z,2E)-5-[1-(2,4-dichlorophenyl)pyrazol-3-yl]¬oxy-2-methoxyimino-N,3-dimethyl-pent-3-enamide |
| M3A-61 | I 1-[4-(4-chlorophenoxy)-2-(trifluoromethyl)phenyl]-1-cyclopropyl-2-(1,2,4-triazol-1-yl)ethanol | (Z,2E)-5-[1-(4-chlorophenyl)pyrazol-3-yl]oxy-2-methoxyimino-N,3-dimethyl-pent-3-enamide |
| M3A-62 | I 1-[4-(4-chlorophenoxy)-2-(trifluoromethyl)phenyl]-1-cyclopropyl-2-(1,2,4-triazol-1-yl)ethanol | trifloxystrobin |
| M3A-63 | I 1-[4-(4-chlorophenoxy)-2-(trifluoromethyl)phenyl]-1-cyclopropyl-2-(1,2,4-triazol-1-yl)ethanol | picoxystrobin |
| M3A-64 | I 1-[4-(4-chlorophenoxy)-2-(trifluoromethyl)phenyl]-1-cyclopropyl-2-(1,2,4-triazol-1-yl)ethanol | azoxystrobin |
| M3A-65 | I 1-[4-(4-chlorophenoxy)-2-(trifluoromethyl)phenyl]-1-cyclopropyl-2-(1,2,4-triazol-1-yl)ethanol | mandestrobin |
| M3A-66 | I 1-[4-(4-chlorophenoxy)-2-(trifluoromethyl)phenyl]-1-cyclopropyl-2-(1,2,4-triazol-1-yl)ethanol | metominostrobin |
| M3A-67 | I 1-[4-(4-chlorophenoxy)-2-(trifluoromethyl)phenyl]-1-cyclopropyl-2-(1,2,4-triazol-1-yl)ethanol | mancozeb |
| M3A-68 | I 1-[4-(4-chlorophenoxy)-2-(trifluoromethyl)phenyl]-1-cyclopropyl-2-(1,2,4-triazol-1-yl)ethanol | chlorothalonil |
| M3A-69 | I 1-[4-(4-chlorophenoxy)-2-(trifluoromethyl)phenyl]-1-cyclopropyl-2-(1,2,4-triazol-1-yl)ethanol | fenpropimorph |
| M3A-70 | I fluxapyroxad | prothioconazole |
| M3A-71 | I fluxapyroxad | difenoconazole |
| M3A-72 | I fluxapyroxad | propiconazole |
| M3A-73 | I fluxapyroxad | tetraconazole |
| M3A-74 | I fluxapyroxad | tebucoanzole |
| M3A-75 | I fluxapyroxad | pyraclostrobin |
| M3A-76 | I fluxapyroxad | (Z,2E)-5-[1-(2,4-dichlorophenyl)pyrazol-3-yl]¬oxy-2-methoxyimino-N,3-dimethyl-pent-3-enamide |
| M3A-77 | I fluxapyroxad | (Z,2E)-5-[1-(4-chlorophenyl)pyrazol-3-yl]oxy-2-methoxyimino-N,3-dimethyl-pent-3-enamide |
| M3A-78 | I fluxapyroxad | trifloxystrobin |
| M3A-79 | I fluxapyroxad | picoxystrobin |
| M3A-80 | I fluxapyroxad | azoxystrobin |
| M3A-81 | I fluxapyroxad | mandestrobin |
| M3A-82 | I fluxapyroxad | metominostrobin |
| M3A-83 | I fluxapyroxad | mancozeb |
| M3A-84 | I fluxapyroxad | chlorothalonil |
| M3A-85 | I fluxapyroxad | fenpropimorph |
| M3A-86 | I pyraclostrobin | prothioconazole |
| M3A-87 | I pyraclostrobin | difenoconazole |
| M3A-88 | I pyraclostrobin | propiconazole |
| M3A-89 | I pyraclostrobin | tetraconazole |

TABLE 3-continued

| "I" is compound I, "II" is compound II" | | |
|---|---|---|
| No | I II | II (2) |
| M3A-90 | I pyraclostrobin | tebucoanzole |
| M3A-91 | I pyraclostrobin | mancozeb |
| M3A-92 | I pyraclostrobin | chlorothalonil |
| M3A-93 | I pyraclostrobin | fenpropimorph |
| M3A-94 | I (Z,2E)-5-[1-(2,4-dichlorophenyl)pyrazol-3-yl]¬oxy-2-methoxyimino-N,3-dimethyl-pent-3-enamide | prothioconazole |
| M3A-95 | I (Z,2E)-5-[1-(2,4-dichlorophenyl)pyrazol-3-yl]¬oxy-2-methoxyimino-N,3-dimethyl-pent-3-enamide | difenoconazole |
| M3A-96 | I (Z,2E)-5-[1-(2,4-dichlorophenyl)pyrazol-3-yl]¬oxy-2-methoxyimino-N,3-dimethyl-pent-3-enamide | propiconazole |
| M3A-97 | I (Z,2E)-5-[1-(2,4-dichlorophenyl)pyrazol-3-yl]¬oxy-2-methoxyimino-N,3-dimethyl-pent-3-enamide | tetraconazole |
| M3A-98 | I (Z,2E)-5-[1-(2,4-dichlorophenyl)pyrazol-3-yl]¬oxy-2-methoxyimino-N,3-dimethyl-pent-3-enamide | tebucoanzole |
| M3A-99 | I (Z,2E)-5-[1-(2,4-dichlorophenyl)pyrazol-3-yl]¬oxy-2-methoxyimino-N,3-dimethyl-pent-3-enamide | mancozeb |
| M3A-100 | I (Z,2E)-5-[1-(2,4-dichlorophenyl)pyrazol-3-yl]¬oxy-2-methoxyimino-N,3-dimethyl-pent-3-enamide | chlorothalonil |
| M3A-101 | I (Z,2E)-5-[1-(2,4-dichlorophenyl)pyrazol-3-yl]¬oxy-2-methoxyimino-N,3-dimethyl-pent-3-enamide | fenpropimorph |
| M3A-102 | I (Z,2E)-5-[1-(4-chlorophenyl)pyrazol-3-yl]oxy-2-methoxyimino-N,3-dimethyl-pent-3-enamide | prothioconazole |
| M3A-103 | I (Z,2E)-5-[1-(4-chlorophenyl)pyrazol-3-yl]oxy-2-methoxyimino-N,3-dimethyl-pent-3-enamide | difenoconazole |
| M3A-104 | I (Z,2E)-5-[1-(4-chlorophenyl)pyrazol-3-yl]oxy-2-methoxyimino-N,3-dimethyl-pent-3-enamide | propiconazole |
| M3A-105 | I (Z,2E)-5-[1-(4-chlorophenyl)pyrazol-3-yl]oxy-2-methoxyimino-N,3-dimethyl-pent-3-enamide | tetraconazole |
| M3A-106 | I (Z,2E)-5-[1-(4-chlorophenyl)pyrazol-3-yl]oxy-2-methoxyimino-N,3-dimethyl-pent-3-enamide | tebucoanzole |
| M3A-107 | I (Z,2E)-5-[1-(4-chlorophenyl)pyrazol-3-yl]oxy-2-methoxyimino-N,3-dimethyl-pent-3-enamide | mancozeb |
| M3A-108 | I (Z,2E)-5-[1-(4-chlorophenyl)pyrazol-3-yl]oxy-2-methoxyimino-N,3-dimethyl-pent-3-enamide | chlorothalonil |
| M3A-109 | I (Z,2E)-5-[1-(4-chlorophenyl)pyrazol-3-yl]oxy-2-methoxyimino-N,3-dimethyl-pent-3-enamide | fenpropimorph |

Thus, the present invention relates to the use of any of the mixtures M3A-1 to M3A-109 as defined in Table 43 for combating resistant fungi on soybean, and the resistant fungi is *Cercospora sojina.*

All above-referred mixtures are herein below abbreviated as inventive mixtures.

The term "use of compound I or any of the inventive mixtures for combating resistant fungi on soybean" comprises a method for controlling resistant fungi on soybean, wherein the fungi, their habitat, breeding grounds, their locus or the plants to be protected against such fungal attack, the soil or plant propagation material (preferably seed) are treated with a pesticidally effective amount of a compound I as defined above or a mixture of compound I with one or two compounds II.

Preferably, such method for controlling resistant fungi on soybean comprises treating the pest, their habitat, breeding grounds, their locus or the plants to be protected against pest attack with a pesticidally effective amount of a compound I as defined above or a mixture of compound I with one or two compounds II.

The term "effective amount" means that compound I or the inventive mixtures are used in a quantity which allows obtaining the desired effect which is a synergistic control of resistant fungi, but which does not give rise to any phytotoxic symptom on the treated plant.

If the compound I is applied with one or two compounds II, such application can be made simultaneous that is jointly or separately, or in succession.

The ratio by weight of compound I and compound II in binary inventive mixtures is from 20000:1 to 1:20000, from 500:1 to 1:500, preferably from 100:1 to 1:100 more preferably from 50:1 to 1:50, most preferably from 20:1 to 1:20, and utmost preferably ratios from 10:1 to 1:10, which also includes ratios of 1:5 to 5:1, 1:1.

The ratio by weight of compound I, II and second compound II in each combination of two ingredients in the mixture of three ingredients is from 20000:1 to 1:20000, from 500:1 to 1:500, preferably from 100:1 to 1:100 more preferably from 50:1 to 1:50, most preferably from 20:1 to 1:20, and utmost preferably ratios from 10:1 to 1:10 including also ratios from 1:5 to 5:1, or 1:1.

Compound I or the inventive mixtures can be accompanied by further pesticides, e.g. one or more insecticides, fungicides, herbicides.

The compound I or the inventive mixtures can be converted into customary types of agrochemical compositions, e. g. solutions, emulsions, suspensions, dusts, powders, pastes, granules, pressings, capsules, dispersions, and mixtures thereof. Examples for composition types are suspensions (e.g. SC, OD, FS), emulsifiable concentrates (e.g. EC), emulsions (e.g. EW, EO, ES, ME), dispersible concentrates (DC), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsitituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I or the inventive mixtures on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkyliso-thiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I or the inventive mixture and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I or the inventive mixture and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I or the inventive mixture and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I or the inventive mixture and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I or the inventive mixture are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I or the inventive mixture are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I or the inventive mixture are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I or the inventive mixture are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a compound I or the inventive mixture are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I or the inventive mixture, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I or the inventive mixture according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound I or the inventive mixture are ground finely and mixed intimately with solid carrier (e.g. finely divided kaolin) ad 100 wt %.

xii) Granules (GR, FG)

0.5-30 wt % of a compound I or the inventive mixture is ground finely and associated with solid carrier (e.g. silicate) ad 100 wt %. Granulation is achieved by extrusion, spray-drying or fluidized bed.

xiii) Ultra-Low Volume Liquids (UL)

1-50 wt % of a compound I or the inventive mixture are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The resulting agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying the compound I or the inventive mixtures and compositions thereof, respectively, on to plant propagation material, especially seeds include dressing, coating, pelleting, dusting, soaking and in-furrow application methods of the propagation material. Preferably, the compound I or the inventive mixtures or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.01 to 1.0 kg per ha, and in particular from 0.05 to 0.75 kg per ha.

In treatment of plant propagation materials such as seeds, e. g. by dusting, coating or drenching seed, amounts of active substance of from 0.01-10 kg, preferably from 0.1-1000 g, more preferably from 1-100 g per 100 kilogram of plant propagation material (preferably seeds) are generally required.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally one or two further active components II as defined herein above.

The invention claimed is:

1. A method for controlling phytopathogenic fungi on soybean comprising treating the fungi, their habitat, breeding grounds, their locus or the plants to be protected against fungal attack, the soil or plant propagation material with an effective amount of 1-[2-[[1-(4-chlorophenyl)pyrazol-3-yl]oxymethyl]-3-methyl-phenyl]-4-methyl-tetrazol-5-one, as compound I, or a composition comprising compound I;

wherein said fungi contains a G143A mutation in the mitochondrial cytochrome b gene conferring resistance to Qo inhibitors.

2. The method of claim 1, wherein the phytopathogenic fungi is *Cercospora* sojina.

3. The method of claim 1, wherein the phytopathogenic fungi is *Corynespora cassiicola.*

4. The method of claim 1, wherein compound I is applied in form of a composition comprising compound I and compound II, wherein compound II is selected from the group consisting of 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, prothioconazole, difenoconazole, propiconazole, tetraconazole, tebucoanzole, mancozeb, chlorothalonil, fluxapyroxad, bixafen, benzovindiflupyr, pydiflumetofen, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-Apyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, penthiopyrad, isopyrazam, pyraclostrobin, (Z,2E)-5-O-(2,4-dichlorophenyl)pyrazol-3-ylhoxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, trifloxystrobin, picoxystrobin, azoxystrobin, mandestrobin, metominostrobin and fenpropimorph.

5. The method of claim 4, wherein compound II is selected from the group consisting of 2-[4-(4-chlorophenoxy)-2-(trifluoromethyl)phenyl]-1-(1,2,4-triazol-1-yl)propan-2-ol, 2-[4-(4-chlorophenoxy)-2-(trifluoromethyl)phenyl]-3-methyl-1-(1,2,4-triazol-1-yl)butan-2-ol, 1-[4-(4-chlorophenoxy)-2-(trifluoromethyl)phenyl]-1-cyclopropyl-2-(1,2,4-triazol-1-yl)ethanol, fluxapyroxad, pyraclostrobin, (Z,2E)-5-[1-(2,4-dichlorophenyl)pyrazol-3-yl]¬oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide and fenpropimorph.

6. The method of claim 4, wherein the ratio by weight of compound I and second compound II is 500:1 to 1:500.

7. The method of claim 4, wherein the ratio by weight of compound I and second compound II is 100:1 to 1:100.

* * * * *